United States Patent [19]

Serwer

[11] Patent Number: 5,041,203
[45] Date of Patent: Aug. 20, 1991

[54] APPARATUS AND PROCEDURE FOR ROTATING GEL ELECTROPHORESIS

[75] Inventor: Philip Serwer, San Antonio, Tex.

[73] Assignee: The University of Texas System, Austin, Tex.

[21] Appl. No.: 393,084

[22] Filed: Aug. 9, 1989

Related U.S. Application Data

[63] Continuation of Ser. No. 212,521, Jun. 28, 1988, abandoned.

[51] Int. Cl.⁵ .................. G01N 27/26; B01D 57/02
[52] U.S. Cl. ........................... 204/299 R; 204/182.8
[58] Field of Search ................... 204/299 R, 182.8

[56] References Cited

U.S. PATENT DOCUMENTS

| | | | |
|---|---|---|---|
| 2,648,636 | 8/1953 | Ellis et al. | 252/303 |
| 2,992,979 | 7/1961 | Magnuson et al. | 204/180 |
| 4,040,940 | 8/1977 | Bier | 204/299 R |
| 4,061,561 | 12/1977 | Fletcher et al. | 204/299 R |
| 4,148,703 | 4/1979 | Trop et al. | 204/180 G |
| 4,432,849 | 2/1984 | Saito | 204/180 R |
| 4,569,741 | 2/1986 | Pohl | 204/186 |
| 4,693,804 | 9/1987 | Serwer | 204/182.1 |

FOREIGN PATENT DOCUMENTS 872133  4/1987  PCT Int'l Appl. .............. 204/299 R

OTHER PUBLICATIONS

Southern et al., "A model for the separation of large DNA molecules by crossed field gel electrophoresis", Nucleic Acids Research, vol. 15, No. 15, pp. 5925–5943 (1987).
The Mechanism of DNA's Fractionation During Pulsed-Field Agarose Gel Electrophoresis: A Hypothesis, Philip Serwer, submitted to the Journal of the Electrophoresis Society.
Pulsed Field Gel Electrophoresis: a technique for fractionating large DNA molecules, R. Anand, Trends in Genetics, vol. 2, No. 11, 278–283, Nov. 1986.
Construction of Long-Range Restriction Maps in Human DNA Using Pulsed Field Gel Electrophoresis, Gemmill et al., 1987, Gene Anal Techn 4: 119–131.
Gel electrophoresis with discontinuous rotation of the gel: An alternative to gel electrophoresis with changing direction of the electrical field, Philip Serwer, Electrophoresis 1987, 8, 301–304.
Fractionation of Large Mammalian DNA Restriction Fragments Using Vertical Pulsed Field Gradient Gel Electrophoresis, K. Gardiner et al., Somatic Cell and Molecular Genetics, vol. 12, No. 2, 185–195 (1986).
Separation of Yeast Chromosome Sized DNAs by Pulsed Field Gradient Gel Electrophoresis, D. Schwartz et al., Cell, Vol. 37, 67–75, May 1984.
Concatemerization and Packaging of Bacteriophage T7 DNA in Vitro; Determination of the Concatemers' Length and Appearance Kinetics by Use of Rotating Gel Electrophoresis, M. Son et al., Virology 162, pp. 38–46 (1988).
Electrophoretic Separations of Large DNA Molecules by Periodic Inversion of the Electric Field, Carle et al., Science, vol. 232, 65–68, Apr. 4, 1986.

(List continued on next page.)

Primary Examiner—John F. Niebling
Assistant Examiner—John S. Starsiak, Jr.
Attorney, Agent, or Firm—Arnold, White & Durkee

[57] ABSTRACT

An apparatus and a procedure for fractionating DNA using agarose gel electrophoresis is provided. To improve resolution by length and conformation, the direction of the electric field impressed upon the sample is changed by rotating the gel. During agarose gel electrophoresis in one mode, a commerically available stepping motor and indexer are used to periodically re-orient to two different positions a gel on a circular disk within a conventional, horizontal, submerged gel electrophoresis apparatus. Because of the homogeneous field used; DNA forms comparatively sharp, undistorted bands. In one of several other modes, involving electrophoresis during periods of both continuous gel motion and stationary gel, the gel is rotated through integer multiples of 360° followed by stationary electrophoresis.

18 Claims, 4 Drawing Sheets

OTHER PUBLICATIONS

Voltage Ramp Pulsed Field Gel Electrophoresis Separation of Large DNA Molecules, C. Cantor, Electrophoresis '86, 161–171, 1986.

Gel Electrophoresis of DNA, Stellwagen, Proceedings of the 1986 Meeting of the Americas Branch of the Electrophoresis Society, 104–136, Mar. 1986.

Patent Cooperation Treaty publication No. WO/84/02001, The Trustees of Columbia University in the City of New York, West 116th Street and Broadway, New York, NY, 10227, Cantor et al., 560 Riverside Drive, New York, NY, 10027, filed Nov. 18, 1983, published May 24, 1984.

Separation of Large DNA Molecules by Contour Clamped Homogeneous Electric Fields, Chu et al., Science, vol. 234, Dec. 19, 1986, 1582–1585.

Separation of chromosomal DNA molecules from yeast by orthogonal-field-alteration gel electrophoresis, Carle et al., Nucleic Acids Research, vol. 12, No. 14, 1984.

Unique Double-Stranded Fragments of Bacteriophage T5 DNA Resulting from Preferential Shear-Induced Breakage at Nicks, Hayward, Proc. Nat. Acad. Sci. USA, vol. 71, No. 5, pp. 2108–2112, May 1974.

Analysis of Restriction Fragments of T7 DNA and Determination of Molecular Weights by Electrophoresis in Neutral and Alkaline Gels, McDonnell et al., J. Mol. Biol. (1977), 110, 119–146.

Separation of Very Large DNA Molecules by Gel Electrophoresis, Fangman, Nucleic Acids Research, vol. 5, No. 3, Mar. 1978.

Use of Gel Electrophoresis to Characterize Multimolecular Aggregates, Serwer, Methods in Enzymology, vol. 130, 1986, pp. 116–132.

Electrophoresis of Duplex Deoxyribonucleic Acid in Multiple-Concentration Agarose Gels: Fractionation of Molecules with Molecular Weights between $2 \times 10^6$ and $110 \times 10^6$, Philip Serwer, Biochemistry, 19, 3001–3004, 1980.

Concatemers in a Rapidly Sedimenting, Replicating Bacteriophage T7 DNA, Serwer et al., Virology, 123, 474–479 (1982).

Stability and In Vitro DNA Packaging of Bacteriophages: Effects of Dextrans, Sugars, and Polyols, Serwer et al., Journal of Virology, vol. 45, No. 2, 665–671, Feb. 1983.

New Techniques for Purifying Large DNAs and Studying Their Properties and Packaging, Schwartz et al., pp. 189–195 (pub.).

Size Dependent Separation of High Molecular Weight Double-Stranded DNA by Means of Gel Electrophoresis, Lishanskaya et al., Biochemical and Biophysical Research Communications, vol. 52, No. 4, 1213–1221 (1973).

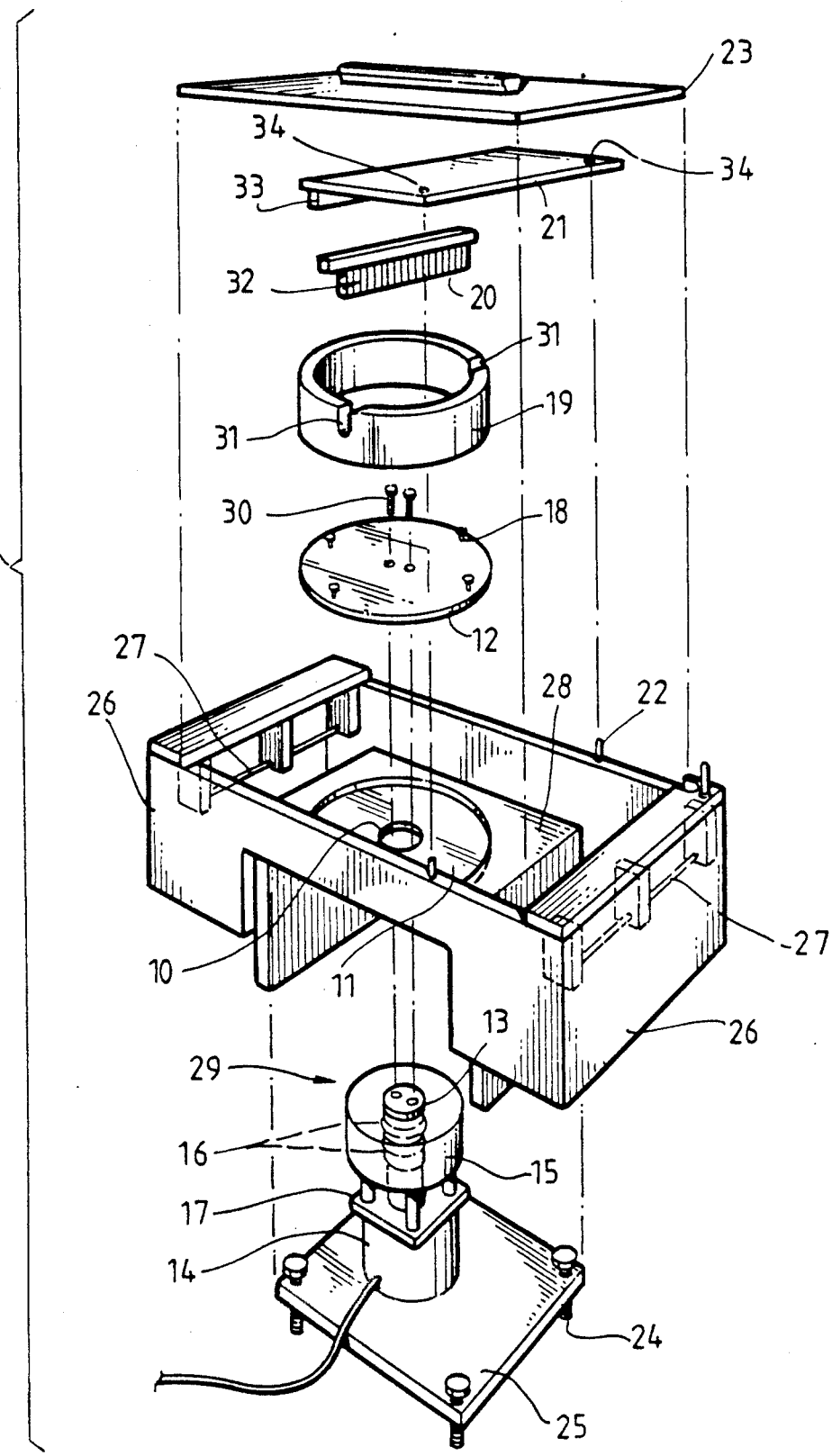

APPARATUS AND PROCEDURE FOR ROTATING GEL ELECTROPHORESIS

Support for the development of the present invention was received from the National Institutes of Health (grants GM24365 and AI22568).

This is a continuation of application Ser. No. 212,521, filed June 28, 1988.

BACKGROUND OF THE INVENTION

The present invention relates generally to the field of electrophoresis. More particularly, but not by way of limitation, the present invention relates to agarose gel electrophoresis in which the direction of the electric field which is impressed upon the sample may be changed either continuously or discontinuously and periodically by rotating the gel during electrophoresis.

The primary purpose for which the present invention was developed was the fractionation of concatemers of T7 DNA. However, the apparatus and method of the present invention are useful in the fractionation of other large DNA molecules and are broadly applicable to any particle that forms either a random coil or a flexible rod.

Although linear, double-stranded DNA is a spherically symmetric random coil in the absence of a gel, the sieving of this DNA during gel electrophoresis suggests that the DNA elongates and migrates end-first during electrophoresis, a process called reptation. Apparently because of reptation, there is a progressive loss in resolution by molecular weight of linear DNA as both the molecular weight and voltage gradient increase.

The detection, isolation, characterization and quantitation of large open circular DNAs are currently of major importance to research and practice concerning both tumor formation and the development of drug-resistant transformed cells. But, discriminating open circular DNA from linear DNA and fractionating open circular DNA by length present problems when known electrophoresis techniques are used. During agarose gel electrophoresis with an electrical field constant in space and time, open circular DNA will eventually completely stop moving as the voltage gradient is raised. This arrest of DNA occurs more easily as the DNA gets longer and is thought to be the result of threading of the DNA by projections from the gel.

The procedures in known electrophoresis techniques with variable fields have included two orthogonally-oriented sets of vertical electrodes that are alternately energized in a horizontal electrophoresis apparatus. More recently, alternate directions of electrophoresis for DNA random coils have been separated by an angle ($\psi$) such that $90 < \psi \leq 180°$. It will be understood that $\psi$ stands for the angle between successive applications of the electric field as viewed from the gel medium, whether this angle is the result of varying the electric field relative to a stationary gel or the result of rotating the gel relative to a single, stationary electric field. For values of $\psi$ other than 180°, either a separate apparatus has to be constructed for each $\psi$, or procedures of voltage clamping have to be used to change $\psi$. To avoid the voltage gradient's nonuniformity at different positions in the gel, a problem that plagued initial procedures, either voltage clamping procedures or an altered electrode arrangement with a laterally buffer-exposed vertical gel have been used.

It is known that by changing the direction of electrical fields with two sets of electrodes, larger DNA molecules can be fractionated than by unidirectional electrophoresis. Schwartz et al., in Separation of Yeast Chromosome-Sized DNAs by Pulsed Field Gradient Gel Electrophoresis, *Cell*, Vol. 37, 67–75, May 1984, describe a system which utilizes perpendicularly oriented, non-uniform, alternately pulsed electrical fields. Using such non-uniform electrical fields, however, results in a distortion of test results, i.e., deformation of bands, and curvature of the path of travel of DNA in the gel, since the forces applied to particles being separated are different for the two directions.

By use of asymmetric times, Carle et al., in Electrophoretic Separations of Large DNA Molecules by Periodic Inverversion of the Electrical Field, *Science*, Vol. 232, 65–68, 1986, used a $\psi$ of 180° for a procedure referred to as Field Inversion Gel Electrophoresis (FIGE). However, when using FIGE, length dispersion of the DNA is less regular, length-mobility inversions occur and the length upper limit is only about 1,000 kb. Chu et al., in Separation of Large DNA Molecules by Contour-Clamped Homogeneous Electric Fields, *Science*, Vol. 234, 1,582–1,585 (1986), changed $\psi$ to 120° and improved field homogeneity by contour clamping a hexagonal device which is otherwise similar to that of Schwartz et al.

Southern et al., in A Model for the Separation of Large DNA Molecules by Crossed Field Gel Electrophoresis, *Nucleic Acids Research*, Vol. 15, No. 15, 5925–5943 (1987), describe an apparatus and method for performing rotating gel electrophoresis (RGE). The apparatus comprises a turntable for the gel driven by a DC motor which is coupled with the turntable through a magnetic drive. On receiving a pulse from a timer, the motor drives the turntable round until it is stopped by a microswitch. At the next pulse, a relay reverses the polarity of the supply to the motor which is driven in the opposite direction until it meets a second microswitch. The microswitches are thrown by pins set in the spindle of the magnetic drive and the pin positions can be altered to alter the angle of the turn. The apparatus allows variation in the angle of the field to the gel, and in the voltage and duration of the DC to the electrodes. The apparatus and method of Southern et al. does not allow for modes of operation with $\psi \geq 360°$ having continuous changes of angle as provided by the present invention. Mention, without description, of the device in Southern et al. was made in Anand, Pulsed field gel electrophoresis: A technique for fractionating large DNA molecules, *Trends In Genet.*, Vol. 2, No. 11, 278–283, November, 1986.

The general advantages of rotating gel electrophoresis (RGE), in comparison to known electrophoresis methods are: (a) Electrical fields are as uniform as they are during normal electrophoresis, without the necessity for any additional procedures such as voltage clamping; (b) there is no restriction on $\psi$; (c) the deformation of bands is no greater than it is during normal electrophoresis; (d) modes with continuous change of angle can be used and (e) gradients of pH are suppressed by buffer tanks (26 in FIG. 1) with a cross-sectional area greater than that of the gel and superposed buffer. In the absence of such buffer tanks, pH gradients are more difficult to suppress by circulation of buffer. For instance, with the apparatus described by Schwartz et al., but not the apparatus used here, electrophoresis using 0.05M sodium phosphate 0.001M $MgCl_2$ resulted in the formation of lines of precipitation in the agarose gel, presumably caused by local alkalinization of the phosphate. This precipitation is hard to suppress by circulation. Because double-stranded DNA does not detectably titrate hydrogen ions between pH's 5 and 9, control of pH for double-stranded DNA is less important than it is for protein-containing particles such as the viruses characterized by agarose gel electrophoresis.

SUMMARY OF THE INVENTION

In known electrophoresis techniques with constant field, test results indicate a progressive loss in resolution by molecular weight as both the molecular weight and voltage gradient increase. To avoid this loss in resolution, in the present invention the direction of the electric field is changed during electrophoresis in several different modes, some discontinuous and other modes including either continuous combined with discontinuous motion or purely continuous motion at variable speed.

To avoid having to either construct a new apparatus or use a different voltage clamping for each $\psi$ used, to simplify the maintaining of uniform conditions of electrophoresis across the gel and to use modes that include a continuous change in angle, the present invention changes the direction of electrophoresis in relation to the gel by rotating the gel (to be referred to as rotating gel electrophoresis, or RGE). The electrophoresis apparatus used is a modified conventional apparatus originally designed for horizontal, submerged agarose gel electrophoresis (to be referred to as normal or conventional electrophoresis), thus simplifying the maintenance of a uniform electrical field and the suppression of pH gradients.

For the procedure of RGE described here, rotation of the gel has been achieved with a stepping motor and indexer obtained commercially. The electrophoresis apparatus is a modified version of an apparatus that in one of several similar forms is sold by many companies. It is possible to assemble all of the components described here without expertise in construction of either the motor or its indexer. The modifications required to be made to a conventional electrophoresis apparatus are in themselves not complicated, and they can be performed without any unusual difficulty by a professional machinist. RGE requires the same level of skill required for the performance of conventional (normal) electrophoresis. Thus, the procedure of RGE described here would be classed as a routine procedure for any laboratory of molecular biology.

In one embodiment of the present invention, (a) the electric field is applied to the gel containing samples, (b) the gel is rotated through an angle $\psi/2$, (c) the gel is rotated through an angle $-\psi$, (d) the gel is rotated through an angle $+\psi$ and (e) steps (c) and (d) are repeated. In a modification of this embodiment, in step (e) the gel is rotated through an angle $360° - \psi$ in the same direction as the previous rotation. In either case, the electric field is applied first in one direction and then another direction displaced from the first direction by an angle $\psi$ such that $90° < \psi \leq 180°$. The net direction of travel of particle samples is along the direction of the bisection of the angle $\psi$. The speed of rotation in this embodiment is relatively fast such as, for example, approximately 100° per second.

In another embodiment of the present invention, the gel is rotated at a relatively slow rate such as, for example, approximately 36° per second while the electric field is applied and gel rotation is continued through integer multiples of 360°. This period of rotation is followed by stationary electrophoresis in the conventional manner. Although the phenomenon is not fully understood, evidence indicates that slow gel rotation in the presence of an electric field causes the leading end of a long DNA molecule to follow the field causing the molecule to be bent into an arc or coil. In one modification of this embodiment, during periods of rotation, the direction of the electric field may be periodically reversed or its magnitude may be changed. In another modification of this embodiment, the gel may first be rotated at a relatively slow rate through 360° in one direction and then through 360° in the opposite direction. Stationary electrophoresis is then performed in the conventional manner. Other embodiments and modifications within the scope of the present invention will be apparent to those of skill in the art.

Work in the general area of the present invention was described by the present inventor in an article in the journal *Electrophoresis* in July, 1987 (hereinafter "*Serwer*").

BRIEF DESCRIPTION OF THE DRAWINGS

The above-noted and other aspects of the present invention will become more apparent from a description of a preferred embodiment when read in conjunction with the accompanying drawings.

The drawings illustrate a preferred embodiment of the invention, wherein like members bear like reference numerals and wherein:

FIG. 1 is an exploded isometric view of an embodiment of the apparatus of the present invention.

DETAILED DESCRIPTION OF A PREFERRED EMBODIMENT

The Apparatus

Figures 2A, 2B, 2C:
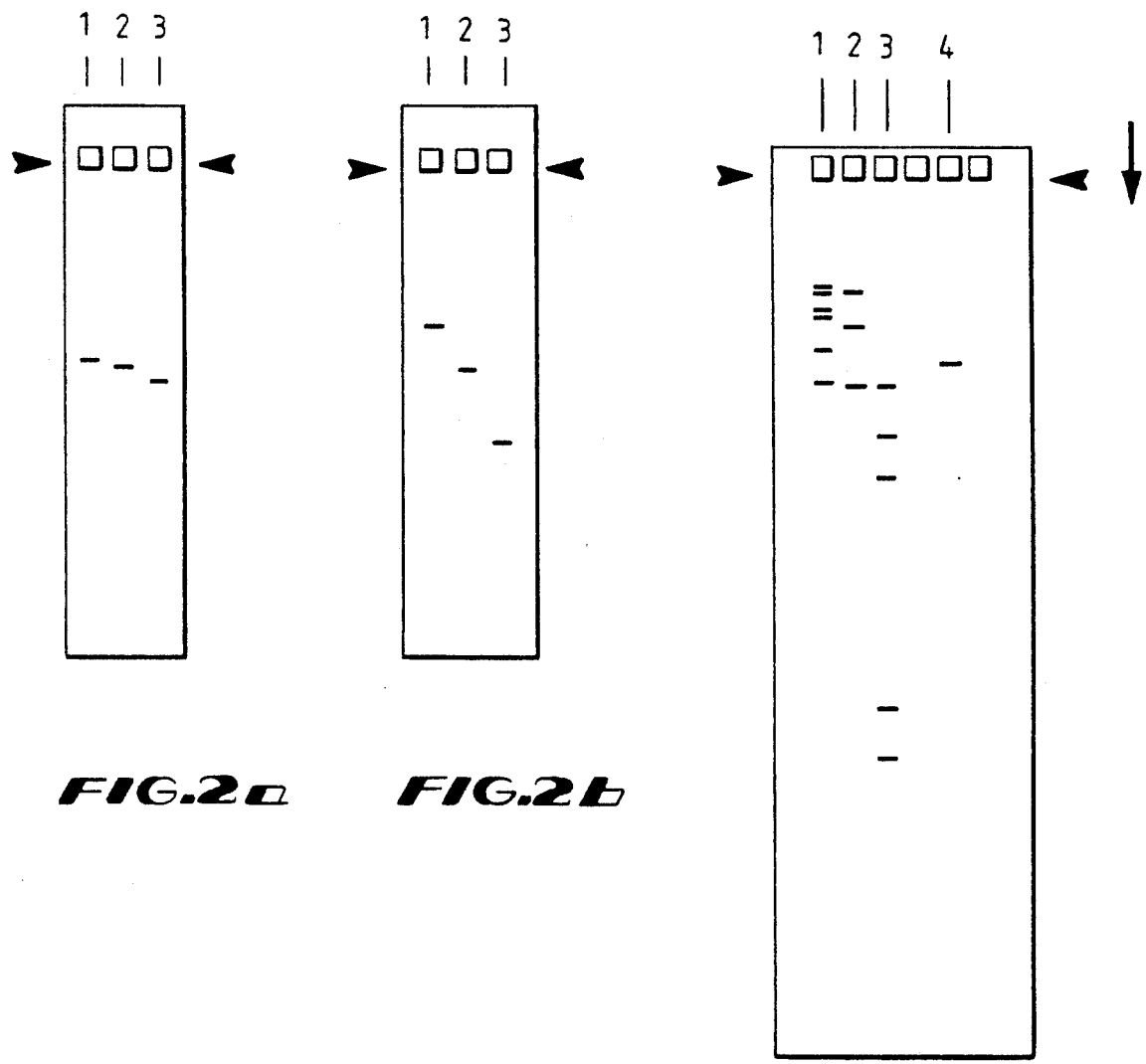
FIG. 2 is a plan view of molecular analyses conducted by rotating gel electrophoresis according to two embodiments of the present invention.

In one aspect, the invention concerns a method of performing multi-dimensional electrophoretic analysis by rotating the electrophoresis gel during electrophoresis.

In a second aspect, the invention concerns an apparatus for conducting rotating gel electrophoresis. The apparatus comprises an apparatus designed for electrophoresis in horizontal, submerged gels, modified for rotation of the gel during electrophoresis. An example of an apparatus that can be modified for an apparatus of the present invention is an Aquebogue Machine and Repair Shop 850 (Aquebogue, N.Y.).

As referred to herein, "program" refers to the selected speed, duration, direction and net angle of rotation during RGE, as well as timing and intensity of the applied electric field.

Referring now to FIG. 1, an apparatus comprising a preferred embodiment is illustrated. A hole 10 is drilled or otherwise formed in raised platform 28 of the apparatus. This hole is sized to accommodate drive shaft 13 of drive assembly 29. When the apparatus of the present invention is assembled, drive shaft 13 is inserted through hole 10 from below. Circular trough 11 is cut or otherwise formed by appropriate means in raised platform 28. The diameter of trough 11 is appropriately sized to accommodate the diameter of gel support disc 12. The depth of trough 11 accommodates the thickness of gel support disc 12 such that, when gel support disc 12 is placed in trough 11, the upper surface of gel support disk 12 is at the plane of the surface of raised platform 28. Hole 10 and trough 11 are concentric.

As previously described, during assembly of the apparatus of the present invention, drive shaft 13 is inserted through hole 10. Gel support disk 12 is placed in trough 11 and concentrically attached to the end of drive shaft 13 by appropriate means such as, for example, screws 30. Gel support disk 12 may also be removably attached to drive shaft 13 by registering holes in the underside of gel support disk 12 with projections on the end of drive shaft 13. The other end of drive shaft 13 is attached to drive means 14. In a preferred embodiment, drive means 14 may be a DC stepping motor, such as model #MOG 1 - F002, purchased from Superior Electric.

Sealed (such as by glue) to the bottom (undersurface) of raised platform 28 is casing 15, in a preferred embodiment made of Plexiglass ®. Casing 15 surrounds shaft 13 between the bottom (underside) of raised platform 28 and the tops of assembly bolts 17. To prevent leakage of buffer from the electrophoresis apparatus, gaskets 16 may be placed between the drive shaft 13 and casing 15, thereby forming a double rotating seal. To improve the seal and lubricate the gaskets 16, they may be coated with silicone high vacuum grease or other appropriate lubricating means.

Drive means 14 in a preferred embodiment is a DC stepping motor. It is attached to the bottom of casing 15 by assembly bolts 17. Means for controlling the stepping motor 14 is also provided as by an indexer, such as, by way of example and not by way of limitation, model PI-55, purchased from Anaheim Automation (Anaheim, Calif.) described more fully below with regard to FIGS. 3 and 4. This indexer rotates drive shaft 13 (and thus gel support disc 12) 0.9 degree each 0.5 step. After the indexer receives an activating signal from the indexer controller, the indexer sends a train of signals to rotate the stepping motor. Switches on the indexer determine the number of half steps and a potentiometer on the indexer determines the rate of stepping. The indexer controller provides control of both the direction of rotation and the delay time between rotations.

Provided on the upper surface of gel support disk 12 are stabilizer screws 18. The shaft of each stabilizer screw 18 prevents horizontal motion of the gel relative to gel stabilizer disk 12 during rotation of the gel. Also, the head of each stabilizer screw 18 helps prevent vertical motion of the gel.

The apparatus is supported on base 25 and can be levelled using levelling screws 24. Lid 23 is provided to reduce evaporation of buffer solution during electrophoresis.

Control Circuits

Figure 3:
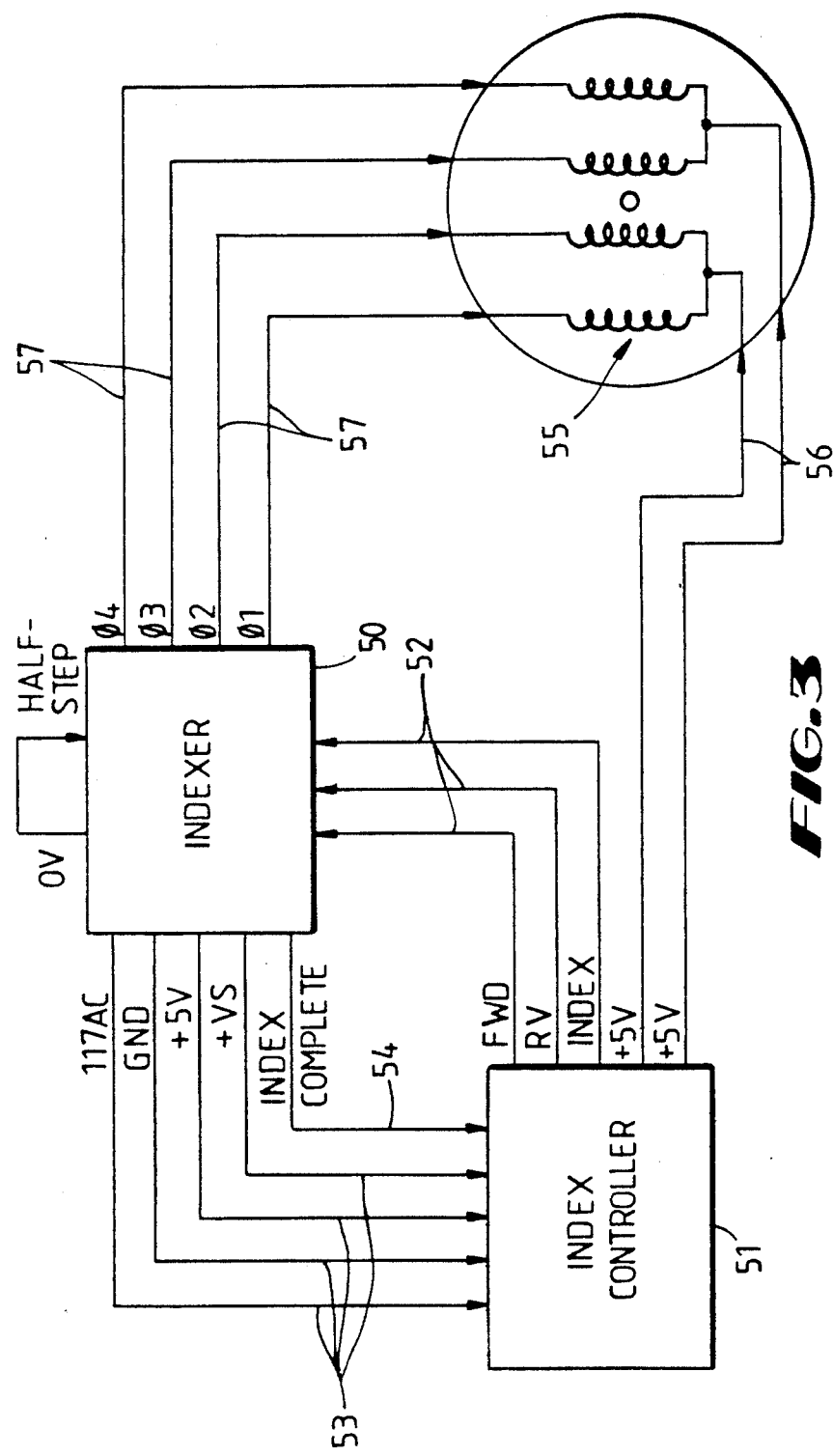
FIG. 3 is a block diagram of the control circuit of the present invention.
Figure 4:
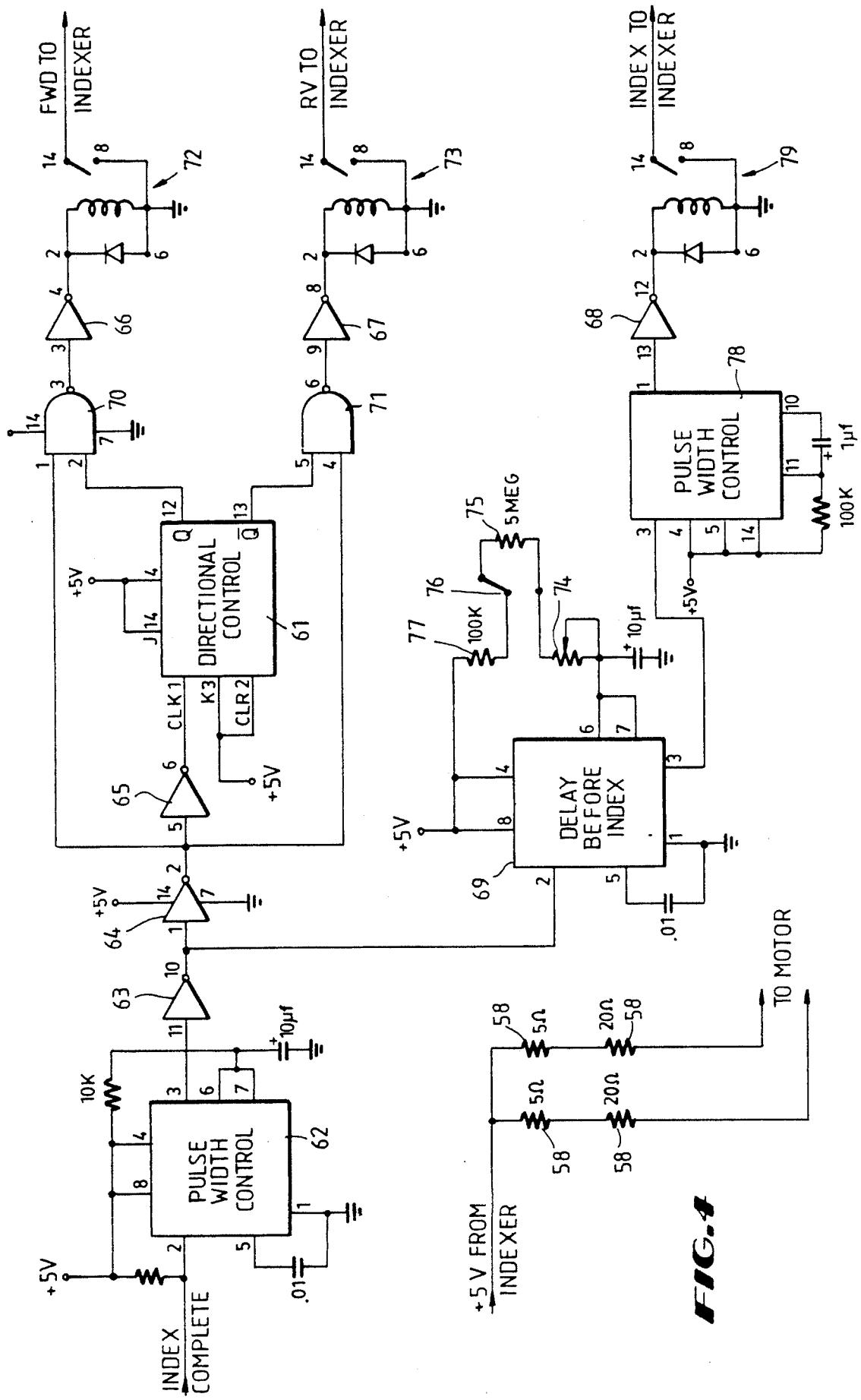
FIG. 4 is a block diagram of the indexer controller in a preferred embodiment of the present invention.

Referring now to FIGS. 3 and 4, the control for a presently preferred embodiment is shown. FIG. 3 is a block diagram of the control circuit external to the DC stepping motor 14. FIG. 4 is a block diagram of the indexer controller 51 of the present invention.

Referring to FIG. 3, indexer controller 51 provides control signals via control lines 52 to indexer 50 which in turn provides power to indexer controller 51 via power lines 53. Indexer 50 also provides a signal to indexer controller 51 that indexing is complete via control line 54. Indexer controller 51 also provides power to the field windings 55 of the DC stepping motor 14 via power lines 56 and the circuit is completed through phase lines 57.

Embodiment #1

FIG. 4 shows embodiment #1 of the present invention. The indexer controller of FIG. 4 was designed to automate the sequencing of the indexer, in a preferred embodiment an Anaheim Indexer PI-55.

Direction control is provided by direction control (J-K) flip-flop 61, in a preferred embodiment a 74LS73. The indexer controller 51 provides direction (forward and reverse) switching and a time delayed signal called Index to start movement of DC stepping motor 14. Plus VS (+28 V) is divided by dropping resistors 58 to limit phase current and provide +5 V to the stepping motor as shown in FIG. 4. Alternating current 117 VAC is used to provide power to a box fan on the indexer controller for cooling the circuits, mainly the dropping resistors. Plus 5 volts and ground provide power to the integrated circuits.

A signal called Index Complete, which occurs when the motor has stopped stepping the angle $\psi$ set on the indexer, starts the sequence. The Index Complete signal is first widened by pulse width control circuit 62 and inverted by inverter 63. Inverters 63, 64, 65, 66, 67 and 68 may be included in one integrated circuit. Inverting the widened Index Complete signal in inverter 63 properly conditions the signal for Delay Before Index circuit 69. The signal is inverted a second time by inverter 64 to provide a properly conditioned signal for NAND gates 70 and 71. The signal is inverted a third time by inverter 65 for proper condition to trigger the direction control flip-flop 61. The direction control circuit then sends a signal to the appropriate NAND gate 70 or 71 to change the direction of rotation of the motor. The signal is then sent to inverter driver 66 or 67 to pick up either relay 72 or relay 73 providing a ground signal for the direction to the indexer 50. Direction control flip-flop 61 changes state each time an index complete signal is received thus changing the direction of rotation of stepping motor 14.

In another mode of operation of this embodiment of the present invention, direction control flip-flop 61 is disabled so that rotation of the gel in each succeeding rotation period is maintained in the same direction. In this embodiment, timing control of the duration of rotation is provided on the indexer such that rotation by an angle $\psi$ is followed by rotation through an angle $360° - \psi$ in the same direction, followed by rotation through an angle $\psi$, etc.

The widened and inverted Index Complete signal from inverter 63 is provided to Delay Before Index circuit 69 as described. Receipt of the signal starts the Delay Before Index Timer counting down as determined by its associated RC network. The time constant of the RC network may be varied by adjustable resistor 74 and by selecting or shorting resistor 75 with switch 76. Adjustable resistor 74 may be, for example, a 500 M$\Omega$ potentiometer. Resistor 77 provides a minimum time for the direction control to take effect before the index signal is sent to pulse width control circuit 78, inverter 68 and to relay 79 to start motor movement Pulse width control circuit 78 provides proper pulse widths after inversion to energize relay 79 which provides a ground signal to indexer 50 to start the motor movement stepping the number of steps set on the indexer.

Embodiment #2

As previously mentioned, the indexer here described rotates drive shaft 13 through 0.9 degree for each half step. Thus, if switches on the indexer are set at 400, then the index complete signal is received after 360° rotation. Up to and including 249 complete 360° rotations can be set on the indexer's switches. The indexer can be modified with switches that turn off direction control. When so modified, successive rotations would be in one direction, either forward or reverse, determined by additional switches on the indexer. Thus, various modes of operating this embodiment are available, as explained more fully below. In embodiment #1, $\psi$ is set greater than 90° but less than or equal to 180° and in embodiment #2, $\psi$ is set for integer multiples of 360°. Also, in embodiment #1, rotation of the gel is relatively fast such as, for example, 100° per second, while in embodiment #2, gel rotation is relatively slow, for example, 36° per second.

Casting Agarose Gels

Referring again to FIG. 1, to contain molten agarose during casting of a gel, ring 19 with a beveled bottom and a diameter equal to that of gel support disk 12 in the gel bed is placed over disk 12. Sample well-forming comb 20 is inserted in notches 31 at the top of ring 19. When sample well-forming comb 20 is in position for casting a gel, each of the bottom ends of tines 32 of comb 20 is positioned above the upper surface of gel support disk 12. For example, there may be approximately 0.2 cm between tines 32 and disk 12. Alignment bar 21 with protrusion 33 is used to orient the comb 20 perpendicular to the sides of raised platform 28. Protrusion 33 slides into notches 31 above comb 20. Alignment holes 34 slide snugly over alignment pins 22 and sample well-forming comb 20 is thereby aligned perpendicular to the sides of raised platform 28.

Molten agarose is next poured inside ring 19 to the desired height such as, for example, 0.5–0.7 cm and allowed to gel. After gelation, the ring 19, comb 20 and alignment bar 21 are removed and the electrophoresis apparatus is filled with electrophoresis buffer to a height above the top of the gel. For example, buffer may extend 0.2–0.4 cm above the gel to completely immerse the gel in buffer.

Templates for embedding multiple agarose gels within one agarose frame (U.S. Pat. No. 4,294,684 to P. Serwer) can be built and used to form such multiple gels on the disk 12 used for RGE.

Application of Apparatus and Method

The following examples demonstrate the application of the apparatus and method of the current invention. Other applications will be immediately apparent to those of skill in the art.

Embodiment #1

Once the gel is formed and immersed in buffer, samples of particles (such as DNA) that are to be separated by RGE may be placed in the sample wells that were formed in the gel. Drive means 14 may then be rotated by $\frac{1}{2} \psi$ to initially position the gel. That is, the arrow in FIG. 2 indicates the direction of electrophoresis (the net direction of travel of sample particles) and the gel will be rotated to $\frac{1}{2} \psi$ on either side of this direction. This initial rotation may be performed under the control of the indexer by halving the setting for $\psi$. The indexer is next set either for reversal of direction for each rotation or for discontinuous and periodic rotation in the same direction. The time between activating pulses for initiation of rotation is also set. RGE is initiated and the setting for $\psi$ is doubled (from its previous setting of $\frac{1}{2} \psi$). Speed of rotation is also selected such as, for example, 100 degrees per second, but this can be varied. During RGE, buffer solution is circulated between buffer tanks 26 to suppress the formation of a pH gradient across the gel. Following RGE, the gel containing separated particles is stained and photographed in the conventional manner as described in Serwer at p. 303.

FIG. 2(b) demonstrates the effect of using RGE in accordance with embodiment #1 of the present invention. FIG. 2(a) illustrates conventional (normal) electrophoresis (i.e., no rotation) and FIG. 2(b) illustrates the result of RGE, at 3 V/cm, with a stationary time of 20 sec., 1.5% agarose gel, with a $\psi$ of 144 degrees at 27° C. The lanes (numbered 1, 2 and 3 in FIG. 2(a) and FIG. 2(b)) contained DNA's from bacteriophages: (1) T4, (2) T5, and (3) T7. The time of electrophoresis was 6 hours in (a) and 18 hours in (b). The arrowheads indicate the origins of electrophoresis and the arrow indicates the direction of electrophoresis.

The improvement in resolution of T7 and T4 DNA's increased as $\psi$ increased from 0 to 153 degrees during RGE by use of embodiment #1. Because $\psi$ can be arbitrarily altered during RGE without introduction of inhomogeneous electrical fields, RGE is considered to be the technique of choice for further investigating the effect of $\psi$ on both the resolution and the time required to achieve separation. The highest ratio of distance migrated by T7 to distance migrated by T4 DNA is 2.29. This ratio is 10% larger than the highest value previously obtained by electrically switching the direction of the electrical field.

Embodiment #2

FIG. 2(c) is a line drawing illustrating RGE by use of another embodiment in which $\psi$ is changed to 360° and the gel is rotated slowly. Evidence indicates that slow rotation causes the leading end of a DNA's random coil to follow the field. The RGE of FIG. 2(c) used embodiment #2 with a stationary time of 10 seconds, a time of rotation of 10 seconds (per 360°), temperature of 10° C., voltage gradient of 3 V/cm and a buffer solution of 0.01 M sodium phosphate, pH 7.4, 0.001M EDTA.

In FIG. 2(c), lane 1 illustrates electrophoresis of a $\lambda$ ladder ($\lambda$ monomer length of 48.5Kb). Beginning at the sample well at the top of FIG. 2(c), the first three sample lines represent particles having 5, 4 and 3 genomes, respectively. The next lower sample line is believed to represent an open circular particle. The last two sample lines represent particles of 2 and 1 genomes, respectively.

Lane 2 of FIG. 2(c) illustrates the results of electrophoresis of T4, T5 and T7 DNA, respectively, as in FIG. 2(a) and FIG. 2(b). Lane 3 illustrates electrophoresis of a $\lambda$ Hind III digest. Sample lines in lane 3, beginning at the sample well: 22Kb, 8.8Kb, 6.1Kb, 2.1Kb and 1.8Kb, respectively. Lane 4 illustrates an intact bacteriophage T3 (i.e., DNA still in capsid), present as a standard.

In this embodiment, evidence indicates that during the 360° rotation the random coil's leading end is bent in a circular arc that has a tail if the DNA is long enough.

Following the 360° rotation and during the period of stationary gel, the DNA will make forward progress, but only after disengaging its circular region. Longer molecules take longer to disengage their circular region than shorter molecules. For even longer molecules, $\psi$ may be set at 720° or even higher integer multiples of 360°.

In this embodiment, other sequences or modes can be used. For example, using the apparatus of the present invention, a time-dependent inversion of the electric field may be applied during circular motion, but not during the stationary periods of electrophoresis. Such field inversion during circular motion weaves the circular region of the random coil in the gel. Another mode of operation within this embodiment involves a series of forward and reverse 360° turns without stopping, followed by stationary electrophoresis. Still another mode of operating this embodiment involves changing the program of rotation from one cycle to the next, including ramping the times during rotations and during stationary electrophoreses. In this and other modes, the time of rotation can be varied independently of the stationary time. The gel may also be rotated for alternating fast and slow periods without a stationary time. In these and other complex modes of operation, the present invention is most easily implemented using a user programmable device, such as a microprocessor, to easily vary the parameters of operation, the speed, direction, duration and net angle of rotation.

By 360° rotation of the gel during electrophoresis, improved resolution of linear DNA is achieved. Further, total arrest of open circular DNA is avoided. By using the apparatus and method of the present invention, the open circular DNA unthreads during gel rotation and then moves forward during the gel's stationary phase, until again threaded. As a circle becomes longer, the time required for arrest during the stationary phase decreases and, therefore, the distance migrated during the stationary phase decreases. Thus, circles are separated by length and the total arrest phenomenon is avoided. By two procedures, either most or all of the linear (and other nonarrested) DNA can be made to migrate more rapidly than the open circular DNA: (a) the time of stationary gel is increased relative to the time of rotating gel (during the time of stationary gel the linear DNA continues to migrate, but the open circular DNA is arrested); (b) the time of stationary gel and rotating gel are increased by the same factor (this eventually causes the reptating linear DNA (i.e., length > 20Kb) to lose length resolution and migrate more rapidly than the open circular DNA). By reducing gel concentration and voltage gradient, this procedure can be tuned to resolve progressively larger circles.

The principles, preferred embodiments and modes of operation of the present invention have been described in the foregoing specification. The invention is not to be construed as limited to the particular forms disclosed, since these are regarded as illustrative rather than restrictive. Moreover, variations and changes may be made by those skilled in the art without departing from the spirit of the invention.

What is claimed is:

1. An apparatus for conducting electrophoretic analyses in an electrophoresis medium while the medium is rotating and while the medium is stopped, the apparatus comprising:

a planar rotatable support to support a medium in which one or more samples of particles to be separated can be placed;

means for generating an electric field which acts on the particles in the medium;

means for rotating the support at controllable and variable speeds, directions, durations and net angle of rotation, the means for rotating the support including means for stopping the support, wherein the means for rotating the support comprises a stepping motor mechanically coupled to the support, an indexer for controlling the speed, direction and duration of movement of the motor, and an indexer controller for providing control signals to the indexer;

containment means for containing a buffer solution at a level above the medium.

2. The apparatus of claim 1 further comprising means for circulating the buffer in the containment means.

3. The apparatus of claim 1 further comprising user programmable means for varying the speed, direction, duration and net angle of rotation.

4. A method for conducting electrophoretic analyses comprising:

forming a gel bed on a rotatable support, said gel bed having sample wells;

placing samples of particles to be separated in the sample wells;

immersing the gel bed in a buffer solution;

periodically rotating the gel bed while applying an electric field at predetermined speeds and directions through an angle that is an integer multiple of $2\pi$ to position the gel bed to a predetermined position for a predetermined duration at said position; and applying an electric field to the gel bed to cause the migration of particles in the samples while the gel bed is at the predetermined position.

5. The method of claim 4 wherein each successive rotation of the gel bed is always in the same direction.

6. The method of claim 4 wherein the time during which the gel is rotated plus the subsequent time during which the gel is stationary defines an interval of rotation and wherein the interval of rotation, speed, direction, and duration of rotation may be dynamically varied from one interval of rotation to the next by means of a user programmable microprocessor.

7. A method for conducting electrophoretic analyses comprising the steps of:

(a) forming a gel bed with sample wells on a rotatable support;

(b) placing particle samples to be separated in the sample wells;

(c) immersing the gel bed in a buffer solution;

(d) energizing the electric field;

(e) periodically rotating the gel through an integer multiple of 360° in the presence of the electric field;

(f) conducting stationary electrophoresis, wherein gel rotation electrophoresis and stationary electrophoresis comprise an electrophoresis step.

8. The method of claim 7 further comprising repeating the electrophoresis step a predetermined number of times.

9. The method of claim 8 wherein gel rotation is performed in the same direction from step to subsequent step.

10. The method of claim 8 wherein the duration of gel rotation is reversed from step to subsequent step.

11. The method of claim 7 further comprising changing the direction of the electric field while rotating the gel.

12. The method of claim 7 further comprising changing the strength of the electric field while rotating the gel.

13. The method of claim 8 wherein the duration of stationary electrophoresis is variable independently of the period of rotation.

14. A method of performing electrophoresis comprising:
 (a) forming a gel bed on a rotatable support, said gel bed having sample wells;
 (b) placing samples of particles to be separated in the sample wells;
 (c) immersing the gel bed in a buffer solution;
 (d) energizing the electric field;
 (e) rotating the gel through 360° in a first direction in the presence of the electric field;
 (f) rotating the gel through 360° in the other direction in the presence of the electric field; and
 (g) performing stationary electrophoresis.

15. The method of claim 14 further comprising repeating steps (f) and (g) a predetermined number of times.

16. The method of claim 14 further comprising periodically repeating steps (f) and (g) a predetermined number of times, wherein each repetition of steps (f) and (g) comprises an electrophoresis step.

17. Electrophoresis apparatus comprising:
 a. a rotatable support for supporting a gel bed, said gel bed having sample wells for holding samples of particles to be separated;
 b. means for immersing the gel bed in a buffer solution;
 c. means for periodically rotating the gel bed while applying an electric field at predetermined speeds and directions through an angle that is an integer multiple of $2\pi$ to position the gel bed to a predetermined position for a predetermined duration at said position; and
 d. means for applying an electric field to the gel bed to cause the migration of particles in the samples while the gel bed is at the predetermined position.

18. The method of claim 4 wherein each successive rotation of the gel bed is always in the opposite direction.

* * * * *

UNITED STATES PATENT AND TRADEMARK OFFICE
CERTIFICATE OF CORRECTION

PATENT NO. : 5,041,203
DATED : August 20, 1991
INVENTOR(S) : Phillip Serwer

It is certified that error appears in the above-identified patent and that said Letters Patent is hereby corrected as shown below:

In column 10, line 67, (CLAIM 10) delete the term "duration" and insert the term --direction-- therefor.

Signed and Sealed this

Nineteenth Day of January, 1993

Attest:

DOUGLAS B. COMER

*Attesting Officer*     *Acting Commissioner of Patents and Trademarks*